United States Patent [19]

McWilliams

[11] Patent Number: 5,513,631

[45] Date of Patent: May 7, 1996

[54] TRIGGERING OF PATIENT VENTILATOR RESPONSIVE TO A PRECURSOR SIGNAL

[75] Inventor: Roger D. McWilliams, San Diego, Calif.

[73] Assignee: Infrasonics, Inc., San Diego, Calif.

[21] Appl. No.: 505,558

[22] Filed: Jul. 21, 1995

[51] Int. Cl.[6] .................................................. A61M 16/00
[52] U.S. Cl. ............................ 128/204.23; 128/204.26; 128/207.18
[58] Field of Search ......................... 128/204.21, 204.23, 128/205.23, 721, 722, 723, 207.18, 204.26

[56] References Cited

U.S. PATENT DOCUMENTS

| | | | |
|---|---|---|---|
| 4,324,259 | 4/1982 | Wright | 128/722 |
| 4,559,953 | 12/1985 | Wright et al. | 128/680 |
| 4,602,644 | 7/1986 | Di Benedetto et al. | 128/207.18 |
| 4,744,356 | 5/1988 | Greenwood | 128/204.23 |
| 4,813,428 | 3/1989 | Muraki et al. | 128/721 |
| 4,860,766 | 8/1989 | Sackner | 128/721 |
| 4,867,152 | 9/1989 | Kou et al. | 128/723 |
| 5,022,402 | 6/1991 | Schieberl et al. | 128/721 |
| 5,052,400 | 10/1991 | Dietz | 128/722 |
| 5,316,010 | 5/1994 | Brown | 128/721 |
| 5,320,092 | 6/1994 | Ryder | 128/205.23 |

*Primary Examiner*—Aaron J. Lewis
*Attorney, Agent, or Firm*—Gregory Garmong

[57] ABSTRACT

A ventilator is operable to ventilate a patient responsive to a trigger signal. A nasal sensor is affixed to the external surface of the nose of the person. A nasal sensor output signal is produced responsive to the alae nasi reflex or other source of nasal movement of the person, and that nasal sensor output signal is provided to a controller, which in turn produces a trigger signal for the ventilator responsive to the nasal sensor output signal. Other sensor signals can also be measured, and used together with the output of the nasal sensor to provide the most reliable triggering and closest synchronization of the mechanical breathing assistance of the ventilator to the spontaneous breathing efforts of the person.

13 Claims, 6 Drawing Sheets

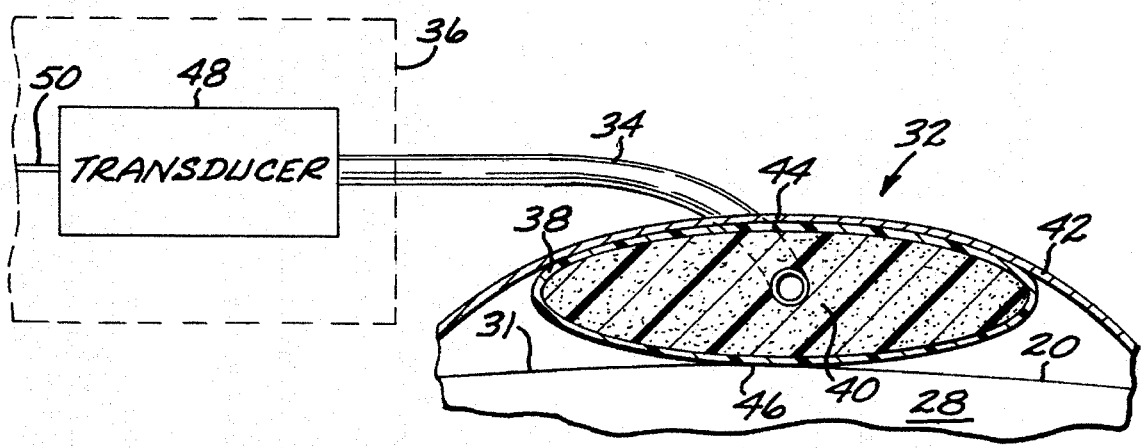
FIG.3
FIG.4
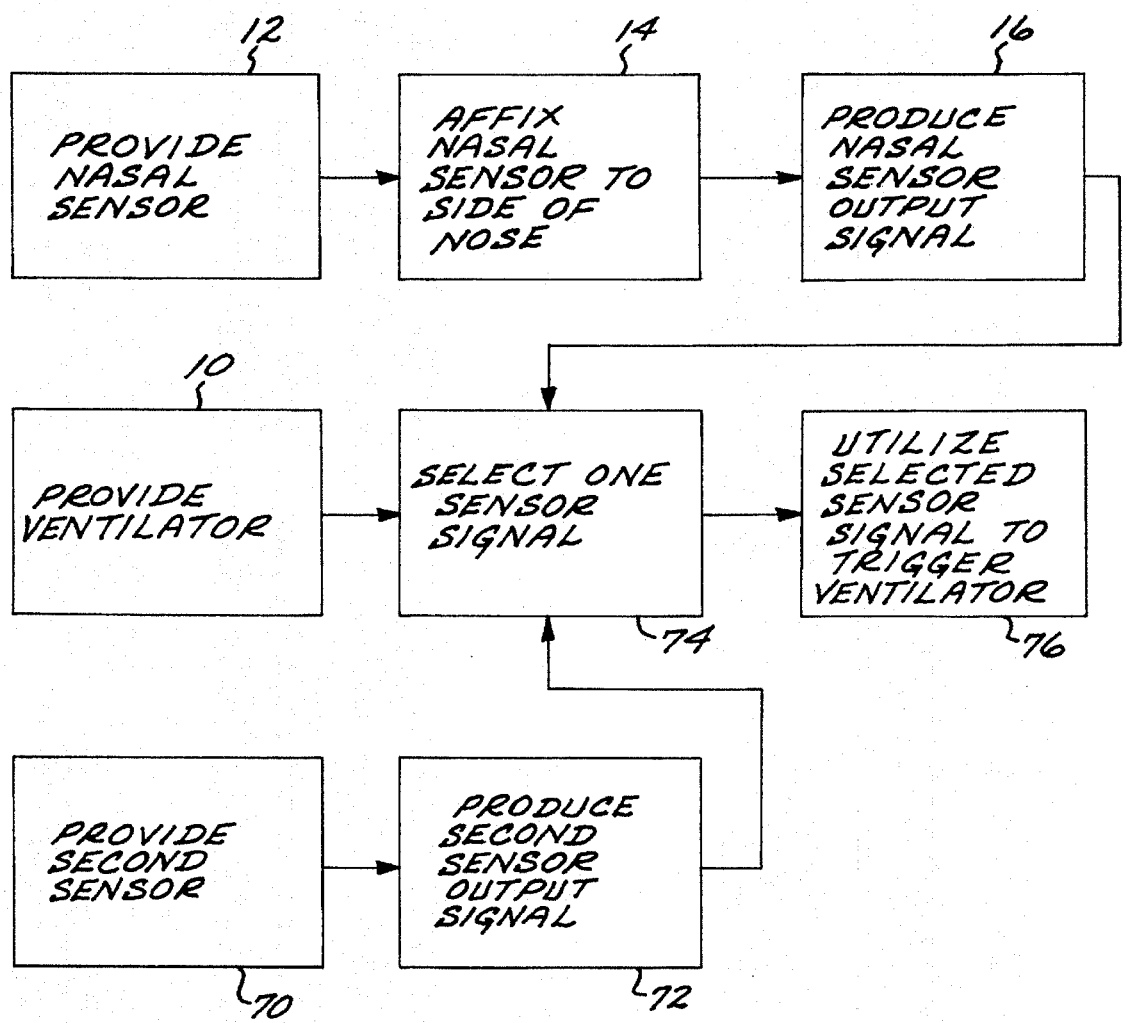

TRIGGERING OF PATIENT VENTILATOR RESPONSIVE TO A PRECURSOR SIGNAL

BACKGROUND OF THE INVENTION

This invention relates to ventilators for use in assisting patients to breathe, and, more particularly, to the triggering of such ventilators responsive to the breathing of the patient.

The condition of a patient who suffers from respiratory difficulties or other health problems can often be remarkably improved simply by ensuring a regular air supply that permits the energy of the patient to be directed elsewhere than obtaining sufficient oxygen. Many ill persons are therefore placed onto a program of breathing assistance with a device called a "ventilator". In simplest terms, the ventilator either forces pressurized gas into the lungs (e.g., a positive-pressure ventilator) or expands the chest cavity to draw gas into the lungs (e.g., a negative-pressure ventilator such as an iron lung) under a selectable schedule of gas composition, pressure, and flow pattern.

Although negative-pressure ventilators enjoyed a degree of popularity in the past, their use has been largely replaced by positive-pressure ventilators. The positive-pressure ventilator is a mechanical device external to the patient, which creates an external pressure and thereby forces gas into the patient's lungs through a tube termed the "airway". The gas may be air, pure oxygen, air enriched with additional oxygen, or some other oxygen-containing mixture.

Where the patient is attempting to breathe on his or her own, termed a "spontaneous breath", under some modes of breathing assistance the operation of the ventilator is synchronized to the spontaneous breathing of the patient so that the ventilator is not forcing gas into the lungs at the same time that the patient is attempting to breathe out. If the operation of the ventilator is not properly synchronized to the breathing of the patient, the ventilator actually works against the spontaneous breathing of the patient. In the absence of proper synchronization, the power of the ventilator can overcome breathing efforts of infants or weakened adults, and can do more harm than good.

To accomplish synchronization of the ventilator to the spontaneous breathing of the patient, a sensor is provided to sense the initiation of a spontaneous breath. The sensor output is used to generate a trigger signal for the ventilator, which then operates to reinforce the spontaneous breath. There is a lag time between the initiation of a spontaneous breath by the patient and the actual flow of gas from the ventilator to the airway, for several reasons. It is therefore important to provide a trigger signal that is as early in time, but after the patient initiates the spontaneous breath, as possible. That is, the sensor should sense the initiation of a spontaneous breath as quickly as possible after the breath is initiated.

Various sensor approaches have been used in the past. One is a pressure or flow sensor placed into the airway of the ventilator. Another type of sensor is a pneumatic sensor placed on the chest of the patient over the diaphragm, so as to sense the first movement of the diaphragm at the start of a spontaneous breath. Electrical sensing of diaphragm and muscle activity have also been used. Studies show that the trigger signal of the airway sensor lags the initiation of a spontaneous breath by a significant period of time. The trigger signals of the pneumatic or electrical diaphragm and muscle sensors lag the initiation of a spontaneous breath by a shorter, but still significant, period of time. Although these types of sensors can provide satisfactory results in some cases, there is an ongoing search for better types of sensors and breathing assistance methods to aid in synchronizing the ventilator to the spontaneous breathing of the patient.

There exists a need for a better approach to the synchronization of a ventilator to a patient's own breathing. Such an improved apparatus would significantly improve the potential for respiratory care of the patients. The present invention fulfills this need, and further provides related advantages.

SUMMARY OF THE INVENTION

The present invention provides a method for triggering a ventilator. This approach permits the triggering of the ventilator more nearly simultaneously with the initiation of a spontaneous breath than possible with conventional approaches. There is, accordingly, reduced likelihood that the ventilator may work against the breathing efforts with the patient. The preferred approach of the invention does not require modification of a standard available sensor. The approach of the invention is not unduly intrusive for the patient being monitored and ventilated. It is also relatively robust and easily used in a typical medical setting.

In accordance with the invention, a method for ventilating a person comprises the steps of providing a ventilator operable to ventilate a person responsive to a trigger signal, and providing a nasal sensor. The nasal sensor is preferably a pneumatic device that senses movement by compression of a constant-volume envelope. The nasal sensor is affixed to the nare (external surface of the side of the nose) of the person. The nasal sensor produces a nasal sensor output signal responsive to the movement of the nare of the person, and the nasal sensor output signal is provided to the ventilator as the trigger signal.

The movement of the nare of the person is responsive to the flaring of the nostril that occurs in some persons and circumstances even before the muscles of the diaphragm initiate the movement of air during the physical drawing of a breath. This movement of the nostril, known as the alae nasi reflex under certain conditions of oxygen deprivation, has been observed as a precursor signal to the act that requires ventilation assistance. It is measurable prior to the time at which diaphragm movement, chest muscle movement, or airway pressure change occurs. The sensing of nare movement therefore gives an early indication of the attempt by the person to draw a spontaneous breath, so that the ventilator may be responsively operated to assist that spontaneous breath.

The inventor has observed, however, that the nasal sensor does not always give the earliest indication of the initiation of a spontaneous breath. Some persons do not exhibit a usable nasal movement reflex. In other persons the nasal movement occurs only in relation to some of the breaths, such as when the person has distressed breathing due to insufficient oxygen or excess carbon dioxide in the blood, or obstructive apnea. The present invention therefore extends to a method for obtaining the best available triggering for any person, during any particular sequence of breaths. In this method, a ventilator is provided. A nasal sensor is also provided, affixed to the nare, and operated to sense a movement of the nare that is a precursor to breathing. A second sensor is also provided that operates responsive to the initiation of a spontaneous breath by the person. The output signals of the nasal sensor and the second sensor are compared as to which provides the earliest (or in some cases, the only) indication of the onset of a spontaneous breath. The earliest indication is used as the basis for a trigger signal to the ventilator.

The present invention provides an advance in the art of ventilator technology. The ventilator is closely synchronized to spontaneous breathing of a person with a smaller time differential than possible with prior sensor approaches. Other features and advantages of the present invention will be apparent from the following more detailed description of the preferred embodiment, taken in conjunction with the accompanying drawings, which illustrate, by way of example, the principles of the invention.

BRIEF DESCRIPTION OF THE DRAWINGS

FIG. 3 is a side sectional view of the sensor of the invention;

FIG. 4 is a process flow diagram for another preferred embodiment of the invention;

DETAILED DESCRIPTION OF THE INVENTION

Figure 1:
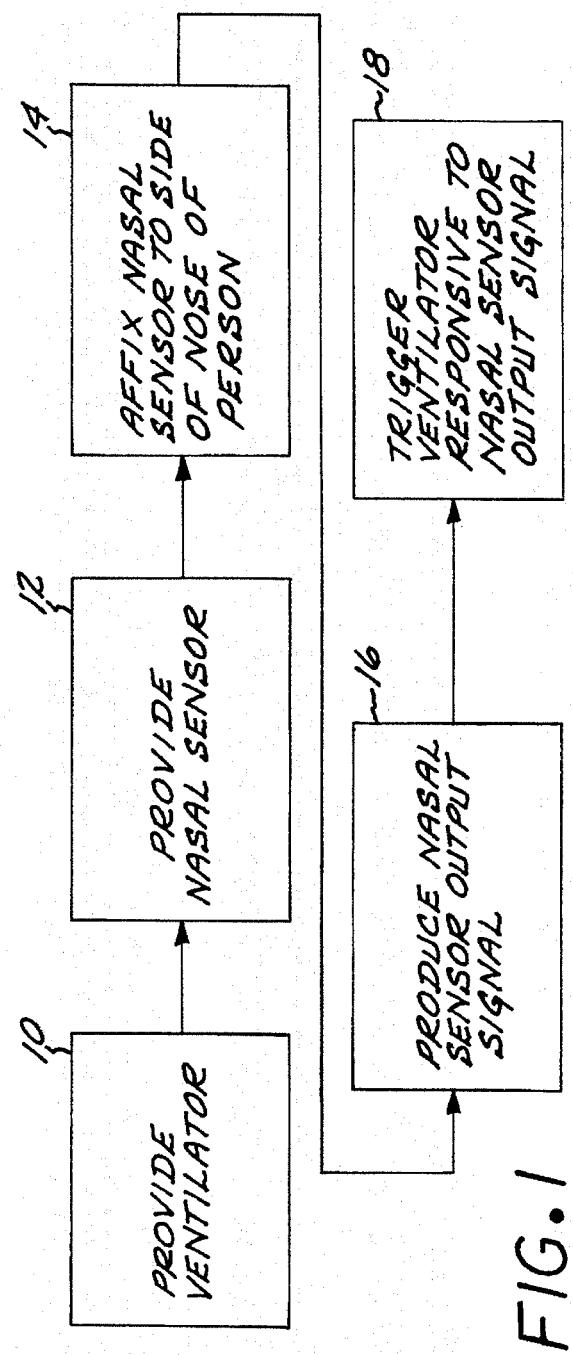
FIG. 1 is a process flow diagram for one preferred embodiment of the invention.
Figure 2:
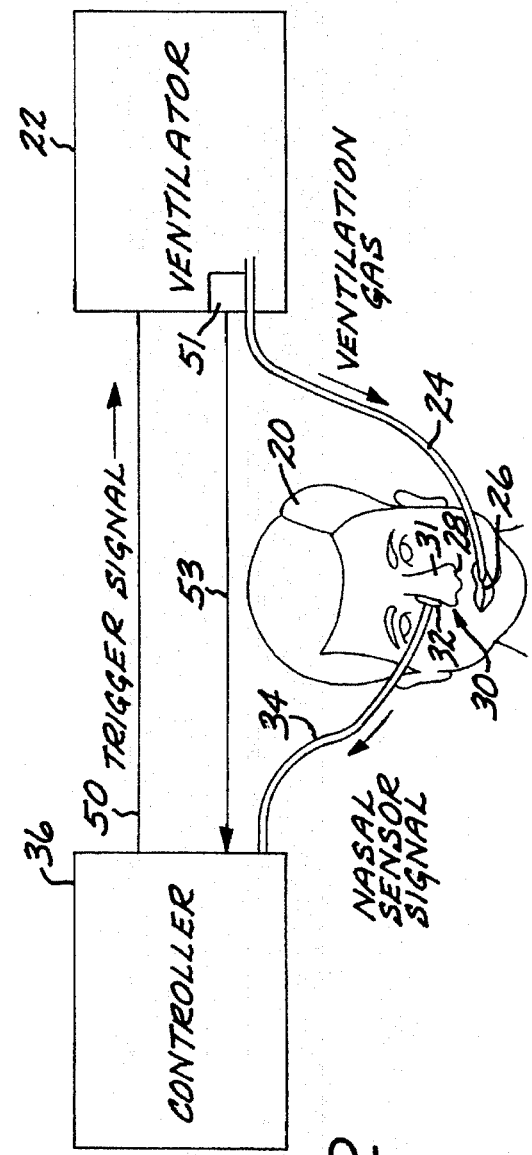
FIG. 2 is a schematic view of the sensor and ventilator as used in relation to a person.

FIG. 1 provides a block flow diagram for one preferred approach of the invention, which can be best understood in relation to a diagrammatic depiction of the apparatus and a person 20 being ventilated in FIG. 2. A ventilator 22 is provided, numeral 10. The ventilator 22 forces pressurized gas through an airway 24 into the person's mouth 26 and thence into the person's lungs. The ventilator 22 is not itself part of the present invention, and may be any acceptable type. Preferred ventilators are the INFANT STAR® ventilator for use with infants and the ADULT START® ventilator for use with adults, both manufactured by Infrasonics, Inc., San Diego, Calif.

When the person 20 attempts to breath by his or her own effort, a "spontaneous breath", in many cases the actual diaphragm movement, airway pressure change, and air flow are preceded by a flaring of the nostrils 28 of the nose 30. Under some conditions, this flaring of the nostrils is known as the alae nasi reflex. It is usually interpreted physiologically as an attempt by the body to minimize the air flow path resistance within the body.

The flaring of the nostrils 28 causes the external surface of the side of the nose 30, the nare 31, to move outwardly. A nasal sensor 32 is provided to sense this movement, numeral 12. The nasal sensor 32 is taped or otherwise affixed to the external surface of the nare 31 of the person 20, numeral 14. A pressure communication tube 34 extends from the interior of the nasal sensor 32 to a controller 36.

The preferred controller 36 is a STAR® SYNC monitor manufactured by Infrasonics, Inc., San Diego, Calif.

The nasal sensor 32 may be of any operable type, but is preferably a pneumatic sensor. A preferred pneumatic nasal sensor 32 is illustrated in more detail in FIG. 3. The sensor 32 is formed as a sealed plastic envelope 38 containing a plastic foam 40. The communication tube 34 communicates with the interior of the envelope 36. The sensor 32 is fastened with a piece of tape 42 to the nare 31 of the person 20, in the manner indicated in FIG. 2.

The piece of tape 42 holds an upper surface 44 of the sensor envelope 38 in a relatively fixed position in respect to the outward movement of the nare 31 of the person. As the nare of the person expands outwardly during the flaring reflex that precedes diaphragm movement, a lower surface 46 of the envelope 38 movements outwardly from the nare 31 of the person 20 (upwardly in the drawing), reducing the volume within the interior of the envelope 38. The pressure within the communication tube 34 increases, and that pressure increase is monitored by a pressure transducer 48 within the controller The transducer 48 produces an electrical nasal sensor output signal 50 proportional to the pressure, numeral 16. Suitable sensors, communication tubes, and transducers (but not their present use) are known in the art and are available commercially. The construction of such a sensor is described in European Patent Specification 0 019 921B.

The nasal sensor output signal 50 is provided to the ventilator 22 as a trigger signal, numeral 18 (FIG. 1). Responsive to this trigger signal 50, the ventilator 22 produces a mechanical breath that is provided to the airway 24 and thence to the lungs of the person 20, to reinforce the spontaneous breath of the person.

Studies of patient breathing by the inventor demonstrate that the nasal reflex is not always present for all persons to give the earliest indication of the initiation of a spontaneous breath by the person. Other sensors may in some cases be advantageously used to trigger the mechanical assistance of the ventilator. Thus, according to another embodiment of the invention depicted in FIG. 4, a ventilator is provided, numeral 10. A nasal sensor is provided, numeral 12, and is affixed to the side of the nose of the person, numeral 14. The nasal sensor produces a nasal sensor output signal, numeral 16. These steps 10, 12, 14, and 16 of FIG. 4 are as described previously in relation to the embodiment of FIGS. 1–3.

Additionally, a second sensor is provided, numeral 70. The second sensor is used to measure the initiation of a spontaneous breath in some other manner. For example, the second sensor could be a pressure sensor used to measure pressure change in the airway 24, an air flow sensor used to measure air flow in the airway, an electrical sensor used to measure muscle contraction in a muscle associated with breathing, as in the chest of the person, or a compression-type pneumatic sensor like the sensor 32 that is applied to another area of the body rather than the rare, such as the abdomen over the diaphragm. The second sensor produces an output signal, numeral 72. One such type of second sensor is illustrated in FIG. 2 as the air flow sensor 51 that measures the gas flow in the airway 24, and which produces the output signal 53 that is provided to the controller 36 for use as will be described. The present approach is operable with other types of second sensors, as well, an important advantage.

The outputs of the nasal sensor and the second sensor are compared, numeral 74, to determine which gives the most reliable and earliest indication of a spontaneous breath by the patient. The comparison may be most easily accomplished with a dual-input oscilloscope or comparable instrument, with the two outputs being compared visually or in an automated fashion. The signal with the earliest rise time to a triggering level would typically be selected. This comparison can be performed in real time with more than one sensor communicating with the person so that the initiation of each mechanical breath can be triggered by any of several sensor inputs. Alternatively, the comparison can be done as an element of the preliminary set-up of the ventilator with the person. In the latter case, one of the sensors would be selected during initial studies of the person, and only that sensor would be used for ongoing sensing of the person.

In either case, the selected signal is used to generate the trigger signal 50 to the ventilator, numeral 76. This provides the person with the most favored source of ventilator triggering during therapy.

The approach of FIG. 4 is a general-form procedure for obtaining synchronization of the mechanical breathing assistance provided by the ventilator with the spontaneous breathing efforts of the person. Based upon observations of patients, some more specific control strategies have been identified.

Figure 5:
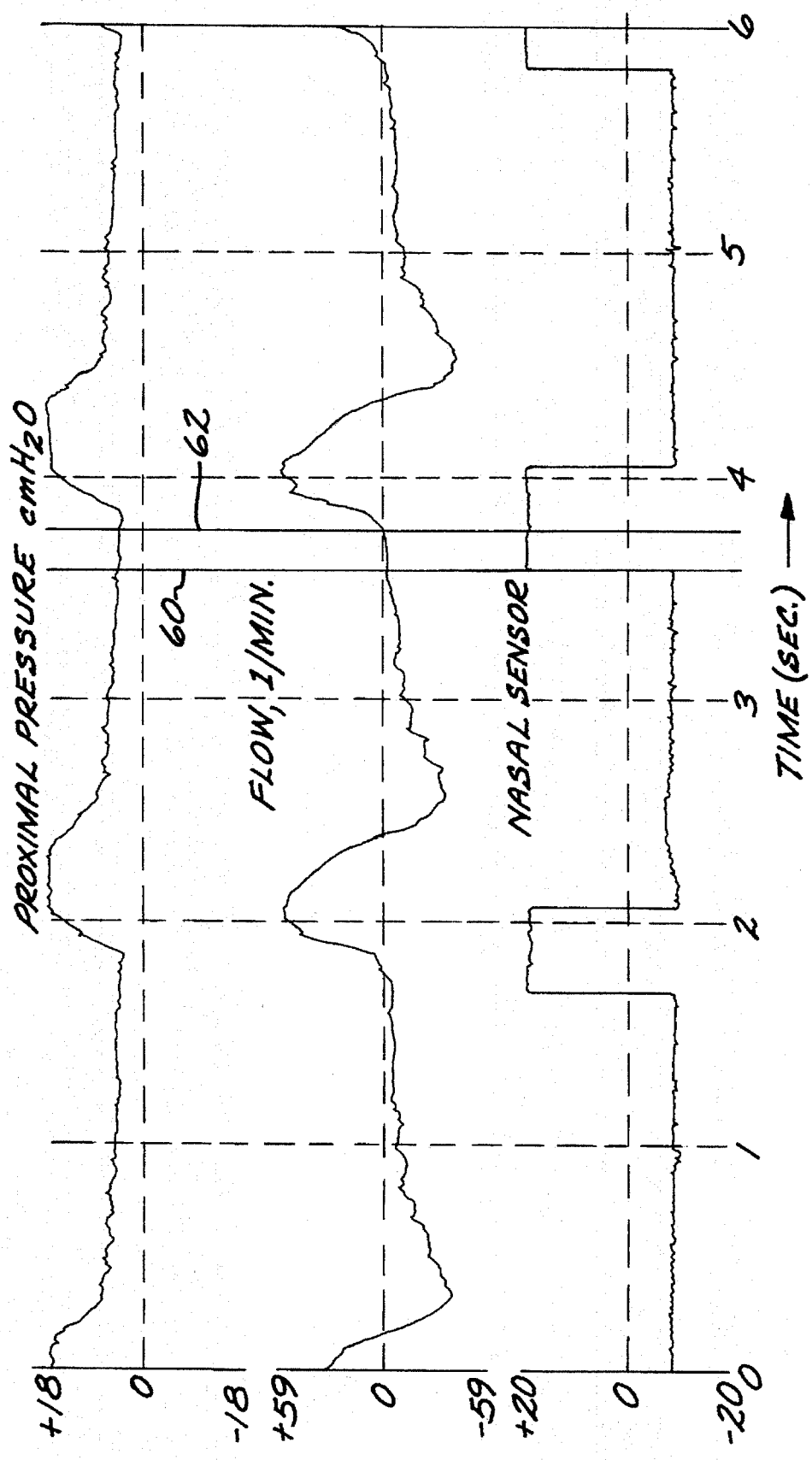
FIG. 5 is a superimposed set of three measured graphs showing airway proximal pressure, air flow, and the initiation and duration of nasal movement of a person.
Figure 6:
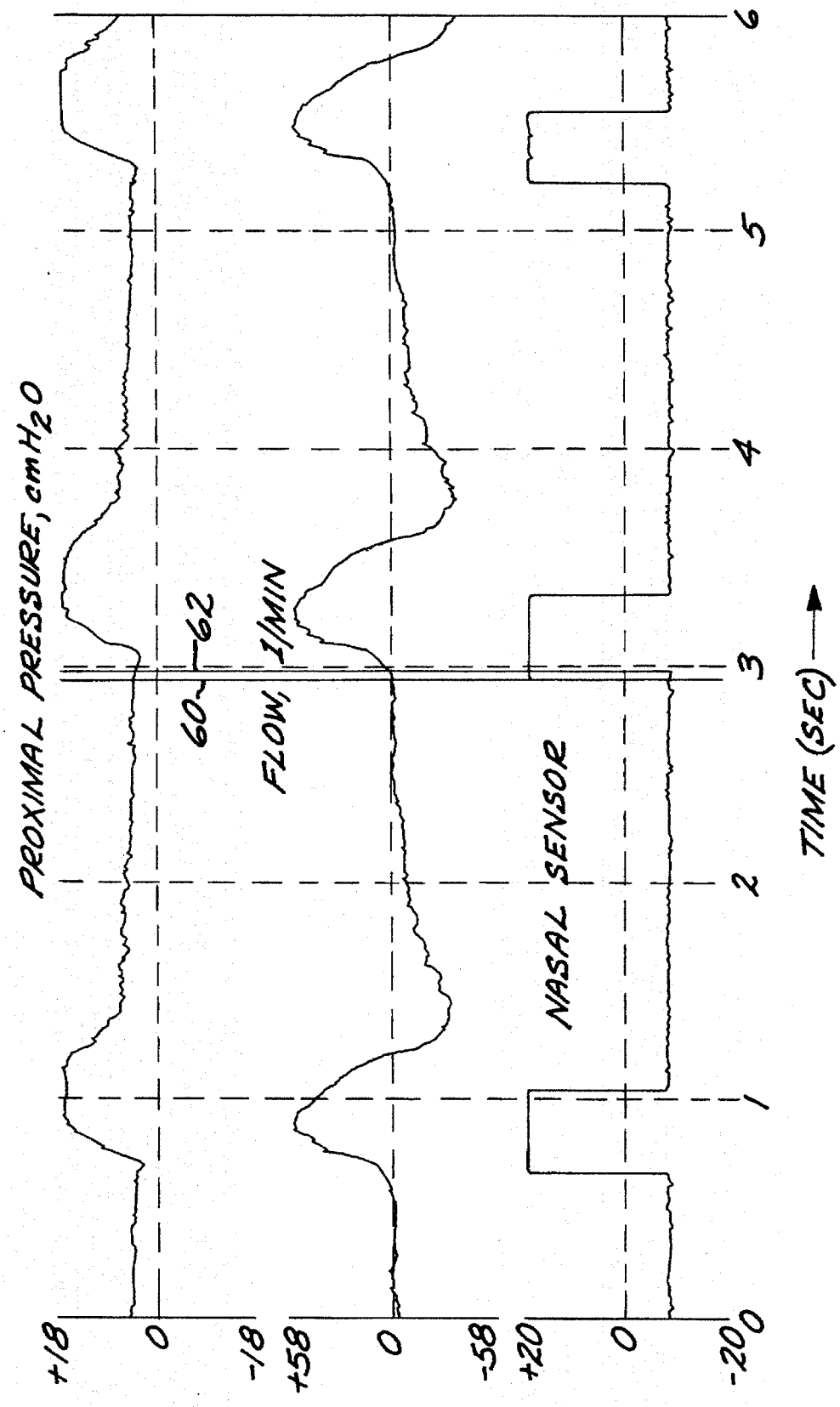
FIG. 6 is a superimposed set of three measured graphs showing airway proximal pressure, air flow, and the initiation and duration of nasal movement of the same person referenced in FIG. 5, in a second time period.

FIGS. 5 and 6 are two sets of superimposed graphs of actual measurements of the breathing of a person and operation of the ventilator, taken at two times during a monitoring period of the same patient. The first set of measurements begins at time t of zero, and the second set begins at time t of about 12 seconds. In each set of graphs, the upper portion is the airway proximal pressure measured by an airway sensor just outside of the person's mouth, the middle portion is the airway flow measured by a flow sensor in the ventilator, and the lower portion shows the initiation and duration of the nasal reflex or flaring.

These figures demonstrate that the use of the nasal response permits triggering of the ventilator prior to the point where it could be triggered responsive to measurements of proximal airway pressure, air flow, or diaphragm movement (which is essentially simultaneous with the first indication of air flow change). The ventilator responds to a trigger signal initiated from the nasal sensor so rapidly that the ventilation may precede the inflow of air responsive to the spontaneous attempt to breathe. Such an early ventilation is potentially as disruptive to patient breathing as a late ventilation that occurs in other situations, because in each case the ventilator is operating against the person's efforts for at least a part of the breathing cycle.

The ability to sense the onset of a spontaneous breath before diaphragm movement, proximal pressure change, or air flow permits the more accurate synchronization of the ventilator to the spontaneous breath. In developing a control strategy, it was necessary first to recognize that the delay between the nasal reflex and the pressure changes and air flow associated with the breath can vary between different persons, or even for a single person within a fairly short period of time.

In FIG. 5, the nasal response from the nasal sensor, numeral 60, precedes the second sensor response associated with diaphragm movement, numeral 62, and the air flow (which begins simultaneously with the first pressure change), by about 0.18 seconds. (The "response" of a sensor, as used herein, is the time at which the sensor generates an output signal according to some selected criterion, such as, for example, first detectable change, half-maximum change, an inflection point, or the like.) By comparison, FIG. 6 shows that, at a different time for the same person, the nasal response 50 precedes the pressure change and air flow 62 by about 0.04 seconds. That is, the physiological delay between the nasal movement and the beginning of spontaneous gas inspiration for the patient varied significantly over a relatively short period of time.

Figure 7:
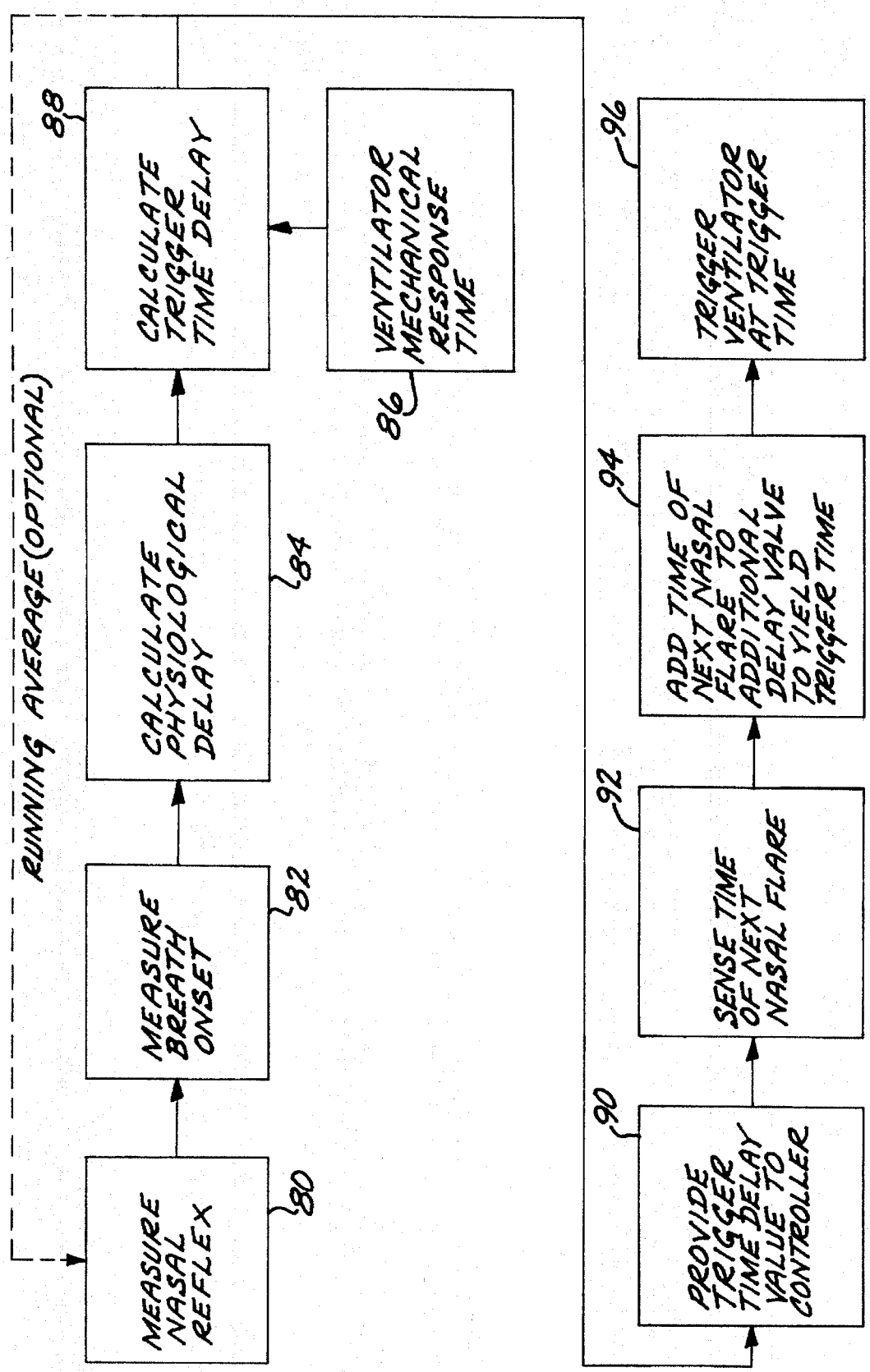
FIG. 7 is a process flow diagram for another preferred embodiment of the invention.

FIG. 7 presents a process flow chart for a procedure for closely synchronizing the ventilator operation with the patient's spontaneous breaths, with virtually no delay and which adjusts the synchronization responsive to the varying physiological delay between the nasal response and the pressure change or air flow. The nasal response is measured, numeral 80, and at least one measurement is made of the onset of inspiration, numeral 82. The measurement 82 could be obtained from a proximal pressure sensor in the airway, a flow sensor in the ventilator, a sensor placed on the abdomen of the patient to measure diaphragm movement, or other operable sensor. The physiological time delay between the nasal response 80 and the measurement of breathing 82 is calculated as their difference, numeral 84.

Figure 8:
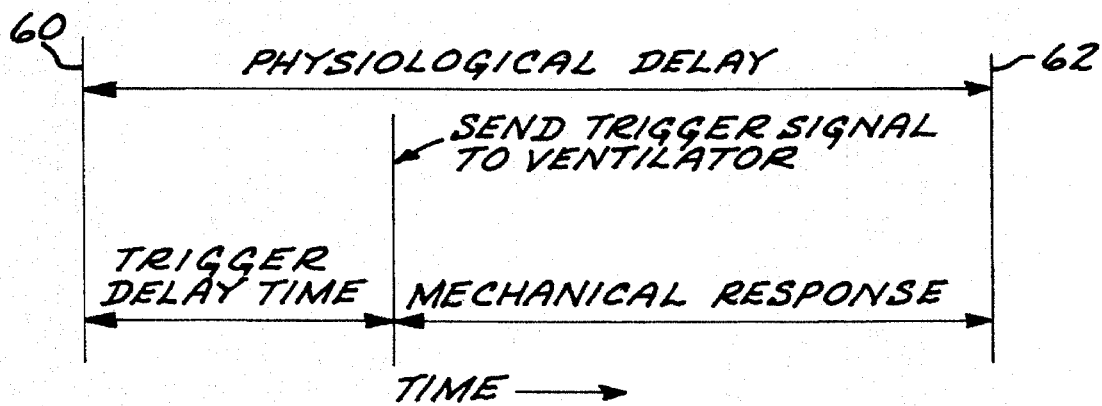
FIG. 8 is a time line graph illustrating the triggering sequence for the mechanical ventilator relative to the drawing of a breath by a person.

FIG. 8 illustrates the time relation between the various measured breathing events and the triggering of the ventilator. Each ventilator is a mechanical device that inherently exhibits a mechanical response time between the time at which its operation is initiated through a trigger signal and the time at which the ventilator begins to move air through the airway. The mechanical response time of the ventilator is known, numeral 86, from the measured characteristics of the ventilator that are supplied by the manufacturer. A required trigger time delay is calculated as the difference between the physiological delay determined in step 84 and the mechanical response time 86, see step 88. This calculated trigger time delay is the additional time that the transmittal of a trigger signal to the ventilator must be intentionally delayed after occurrence of the nasal reflex in order to precisely synchronize the ventilator-produced breathing assistance exactly with the spontaneous attempt to breathe made by the person.

The trigger time delay 88 may be calculated for the single preceding breath made by the person and used in the triggering process of the ventilator for the next breath. Alternatively, a running average for two or more breaths can be made to minimize the effects of electrical fluctuations and the like. This determination may be made either from an analysis of the preceding breaths by the controller, or according to the judgment of a respiratory therapist. If the particular person is exhibiting rapid fluctuations in the calculated physiological delay 84 (e.g., a large difference in the delay 84 over a small number of breaths), the controller or respiratory therapist would preferably choose to use either the single preceding breath or a few preceding breaths for the determination of the trigger time delay 88. If that calculated physiological delay 84 is not fluctuating rapidly, a running average over some larger number of breaths, such as eight breaths, could be used.

A particular advantage of the present invention is that, by using as one control input a breathing precursor signal such as nasal flaring, there is the capability for the initiation of the mechanical breath provided by the ventilator to be adjusted to coincide with the spontaneous effort made by the person. By contrast, when the ventilator is controlled only by measurements made simultaneously with the spontaneous breathing movement of the person, the mechanical response time of the ventilator can never be fully compensated and its effect negated.

Once the value of the trigger time delay 88 has been determined and provided to the controller, on the next succeeding breath the nasal flare sensor movement is measured and its time determined, numeral 92. The trigger time delay 88 is added to the time sensed in step 92, numeral 94. The controller sends the trigger signal 50 to the ventilator at this time, numeral 96 and FIG. 8, so that the mechanical breathing assistance is provided to the person at precisely the correct time.

There is, however, one further complicating consideration in the use of the nasal flare to generate the trigger signal for the ventilator. In a sequence of breaths by some persons, it has been observed by the inventor that occasionally a spontaneous breath can occur without any nasal flare. If the ventilator is triggered solely responsive to the nasal flare, there would be no mechanical breathing assistance for the occasional spontaneous breath where there is no nasal flare.

Figure 9:
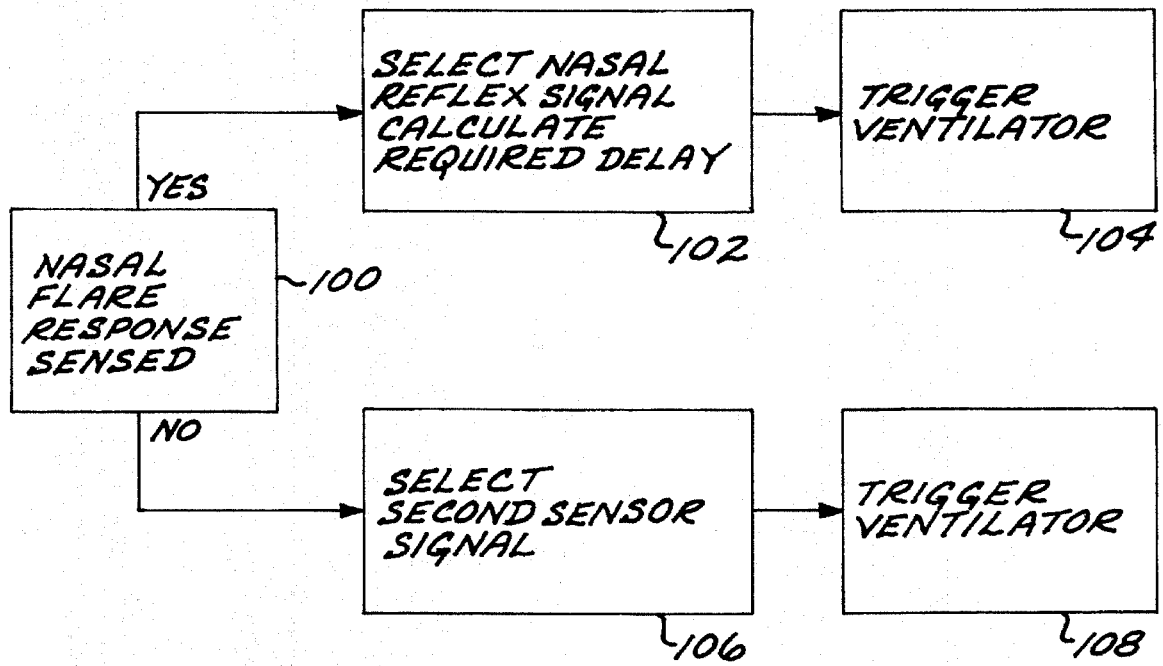
FIG. 9 is a process flow diagram for an alternative triggering approach for a single breath.

To provide assistance in this case, a control approach illustrated in FIG. 9 is used. As discussed before, a first sensor is provided for nasal flare, and a second sensor is provided for breathing initiation (proximal pressure, flow, diaphragm movement, etc.) . The controller determines whether a nasal flare first sensor signal has preceded a breathing initiation second sensor signal, numeral 100, by evaluating whether there has been a first sensor signal within some preselected period prior to the second sensor signal. If there has been a nasal flare first signal (path Y in FIG. 9), which occurs in most instances, the procedure of FIG. 7 is followed, numeral 102, and the ventilator is triggered accordingly, numeral 104. If, however, no such nasal flare signal is detected (path N in FIG. 9), which occurs occasionally, the second sensor signal responsive to the onset of the person's spontaneous breath (e.g., diaphragm movement, proximal pressure, air flow, etc.) is selected, numeral 106, and used to trigger the ventilator, numeral 108. The N path of FIG. 9 will not produce as good a synchronization of the mechanical breathing assistance with the person's spontaneous breathing as the Y path, but it is better than no assistance at all. Thus, for most breaths the ventilator will be triggered by the nasal sensor based, delay-adjusted procedure of FIG. 7, which provides substantially perfectly synchronized mechanical breathing assistance. Occasionally, however, where no nasal reflex occurs, the breath will be provided responsive to the second sensor signal and will have a slight delay time.

The present invention provides for the synchronization of mechanical ventilator operation with the efforts of the person to breathe in a spontaneous manner. This synchronization approach can be used in conjunction with, and is fully consistent with, any of the numerous ventilation modes that have been developed by respiratory in various therapists to assist persons in various circumstances, where the mechanical ventilator is in any way synchronized with the person's own breathing. Some examples of such modes include Assist/Control Ventilation, Assisted Mechanical Breathing, Intermittent Mandatory Ventilation, Synchronized Intermittent Mandatory Ventilation, Continuous Positive Airway Pressure, Airway Pressure Release Ventilation, Pressure Support Ventilation, Mandatory Minute Ventilation, Volume-Assured Pressure Support and combinations involving these modes. The use of the invention is not limited to these modes of ventilation, but instead is applicable to all such synchronized approaches The present invention thus provides an advance in the art of ventilator-assisted breathing of persons. Although p articular embodiments have been described in detail for purposes of illustration, various modifications and enhancements may be made without departing from the spirit and scope of the invention. Accordingly, the invention is not to be limited except as by the appended claims.

I claim:

1. A method for ventilating a person, comprising the steps of:

providing a ventilator operable to ventilate a person responsive to a trigger signal, and a controller that outputs a trigger signal to the ventilator;

providing a nasal sensor;

affixing the nasal sensor to the nare of the person;

producing a nasal sensor output signal of the nasal sensor responsive to the movement of the nare of the person; and providing the nasal sensor output signal to the controller for use in generating the trigger signal.

2. The method of claim 1, wherein the step of providing a nasal sensor includes the step of providing a pneumatic sensor.

3. The method of claim 1, including the additional steps of:

providing a second sensor, producing a second sensor output signal responsive to a spontaneous breath of the person, and providing the second sensor output signal to the controller.

4. The method of claim 3, wherein the step of providing a second sensor includes the step of providing a pneumatic sensor.

5. The method of claim 3, wherein the step of providing the nasal sensor output signal includes the step of utilizing the nasal sensor output signal and the second sensor output signal to determine the trigger signal.

6. The method of claim 3, wherein the step of providing the nasal sensor output signal includes the step of selecting at least one of the nasal sensor output signal and the second sensor output signal to generate the trigger signal.

7. The method of claim 6, wherein the step of selecting includes the step of selecting the one of the nasal sensor output signal and the second sensor output signal which gives the most reliable indication of a spontaneous breath by the patient.

8. A method for ventilating a person, comprising the steps of:

providing a ventilator operable to ventilate a person responsive to a trigger signal, and a controller that outputs a trigger signal to the ventilator;

providing a nasal sensor;

affixing the nasal sensor to a hare of the person;

providing a second sensor;

producing a second sensor output signal responsive to a spontaneous breath of the person;

utilizing the nasal sensor and the second sensor to determine a trigger time at which the trigger signal is to be transmitted by the controller to the ventilator; and transmitting the trigger signal from the controller to the ventilator at the trigger time.

9. The method of claim 8, wherein the step of providing a nasal sensor includes the step of providing a pneumatic sensor.

10. The method of claim 8, wherein the step of providing a second sensor includes the step of providing a sensor selected from the group consisting of a pressure sensor, an air flow sensor, an electrical sensor, and a pneumatic sensor.

11. The method of claim 8, wherein the step of utilizing includes the step of calculating a physiological delay between a response of the nasal sensor and a response of the second sensor, during a first breathing period;

subtracting from the physiological delay a mechanical ventilator response time to determine a trigger time delay;

measuring the response time of the nasal sensor during a spontaneous breath initiated after the first breathing period; and determining the trigger time for the spontaneous breath as the response time of the nasal sensor associated with the spontaneous breath plus the trigger time delay.

12. The method of claim 11, wherein the step of calculating a physiological delay includes the step of calculating the physiological delay based upon a single breath of the person.

13. The method of claim 11, wherein the step of calculating a physiological delay includes the step of calculating the physiological delay based upon an average value determined for a number of breaths of the person.

* * * * *